(12) United States Patent
van den Berg

(10) Patent No.: US 7,473,323 B2
(45) Date of Patent: *Jan. 6, 2009

(54) METHOD AND APPARATUS FOR CLEANING A MILK LINE SYSTEM

(75) Inventor: Karel van den Berg, Bleskensgraaf (NL)

(73) Assignee: Maasland N.V., Maasland (NL)

( * ) Notice: Subject to any disclaimer, the term of this patent is extended or adjusted under 35 U.S.C. 154(b) by 714 days.

This patent is subject to a terminal disclaimer.

(21) Appl. No.: 09/993,961

(22) Filed: Nov. 27, 2001

(65) Prior Publication Data

US 2002/0119574 A1 Aug. 29, 2002

Related U.S. Application Data

(63) Continuation-in-part of application No. 08/707,517, filed on Sep. 4, 1996, now Pat. No. 6,323,033.

(51) Int. Cl.
*B08B 7/04* (2006.01)
*B08B 9/02* (2006.01)

(52) U.S. Cl. .................. 134/18; 134/22.1; 134/22.13; 134/25.3; 436/55; 205/789

(58) Field of Classification Search .............. 134/18, 134/22.11, 22.13, 22.19, 25.2, 22.1, 22.14; 436/23, 55; 205/787, 187, 789

See application file for complete search history.

(56) References Cited

U.S. PATENT DOCUMENTS

| | | | | | |
|---|---|---|---|---|---|
| 3,916,923 A | * | 11/1975 | Branton | .................... | 134/57 R |
| 4,051,059 A | * | 9/1977 | Bowing et al. | .......... | 252/186.23 |
| 5,415,192 A | * | 5/1995 | Pera | ........................ | 134/104.1 |
| 5,567,444 A | * | 10/1996 | Hei et al. | .................... | 424/616 |
| 6,323,033 B1 | * | 11/2001 | van den Berg | ................ | 436/23 |

FOREIGN PATENT DOCUMENTS

DE 3424711 * 2/1986

* cited by examiner

*Primary Examiner*—Michael Barr
*Assistant Examiner*—Saeed T Chaudhry
(74) *Attorney, Agent, or Firm*—Howrey LLP

(57) ABSTRACT

A method and apparatus for cleaning and disinfecting a milk line system and for determining the extent to which a milk line system is rinsed with a cleaning fluid, whereby in one or more places in the milk line system the electric conductivity of the cleaning fluid is determined. More in particular, according to the invention, the electric conductivity is measured in places which are difficult for the cleaning fluid to reach or at places in the milk line system which are more likely to harbor undesirable microbes. The cleaning solutions may be an alkali, detergent, hydrogen peroxide, or acid including peracetic acid, ozone, an alcohol, an aldehyde including formaldehyde, phenol and ethylene oxide, to the extent that these substances do not adversely affect materials such as the compositions of the teat cups.

4 Claims, 1 Drawing Sheet

METHOD AND APPARATUS FOR CLEANING A MILK LINE SYSTEM

RELATED APPLICATION

This is a Continuation-in-Part application of application Ser. No. 08/707,517, filed Sep. 4, 1996, which issued at U.S. Pat. No. 6,323,033 Nov. 27, 2001.

FIELD OF THE INVENTION

The invention relates to a method of cleaning a milk line system of a dairy farm.

BACKGROUND OF THE INVENTION

Milk line systems of dairy farms should be cleaned periodically to prevent milk discharged by the milk line system from being contaminated. With conventional milking machines, the milk line system is cleaned after the herd has been milked. However, with an automated milking system wherein the milking is accomplished with a milking robot, the milk line system is cleaned after a predetermined period of time has elapsed or a predetermined number of animals has been milked. Furthermore the milk line system may also be cleaned when it has been ascertained that milk produced by an animal which is infected with mastitis is being discharged by the line.

The cleaning of the milk line system is divided into three phases which comprise: the pre-rinsing, the main cleaning and the post-rinsing. The pre-rinsing serves to remove the milk residues as much as possible from the lines and the equipment prior to the main cleaning. Consequently, the main cleaning will require less detergent or other cleaning materials. To achieve this, the pre-rinsing step should not be a circulation rinsing. For the pre-rinsing step the water temperature is in the range of 40° C. to 60° C. The pre-rinsing step is succeeded by the main cleaning step. The main cleaning step serves to clean and disinfect the milk line and the milking equipment. This result is obtained by circulating cleaning fluid through the lines and the milking equipment. The main cleaning is normally effected with an alkali having a cleaning and disinfecting function. To avoid formation of scale in the milk line system, said system is normally further cleaned from time to time with an acid. With the acid, scale formed in the milk line system, such as on the electrodes of a milk conductivity sensor, can be dissolved and thus removed from the milk line system. After the main cleaning, the milk line system is normally cleaning by a third step of post-rinsing. This is to prevent residues of the cleaning fluid from coming into the milk. The post-rinsing is generally effected with tap water and the post-rinsing water should preferably not be circulated.

In practice the cleaning of the milk production equipment including milk lines is not carried out correctly as a result of which the equipment and lines are cleaned insufficiently and consequently the germ count of the milk often more than doubles. This may be caused by an insufficient quantity of alkali or acid, or by the insufficient post-rinsing, or by the fact that certain places are not reached by the cleaning fluid, because, for example, a tube is pinched off.

The invention is to provide a method, in which the above-mentioned drawbacks do not occur or are of at least minimized to a considerable extent.

SUMMARY OF THE INVENTION

In accordance with the invention, this is achieved by means of a method of determining the extent to which a milk line system is rinsed with a cleaning fluid, whereby in one or more places in the milk line system the electric conductivity of the cleaning fluid is measured, after which the purity of the cleaning fluid is defined. In this manner, the cleaning of the milk line system is verified. This verification will avoid an insufficient cleaning of the milk line system and an increased germ count of the milk.

According to a method in accordance with the invention, in places where cleaning fluid is difficult to reach or in places in the milk line system which are difficult to clean, or both, the electric conductivity of the cleaning fluid is measured.

According to a further method in accordance with the invention, the electric conductivity is measured in a line connected to a teat cup. In practice this place is one that has found more likely to be contaminated.

According to a further inventive feature, on the basis of the results of the electric conductivity measurement, the concentration of the solvent present in the cleaning fluid or its activity otherwise are determined. On the basis of the measured results it can be checked whether the concentration or activity or both are insufficient or excessive. The solvent added to the cleaning fluid is preferably hydrogen peroxide or peracetic acid, but also may be another acid or an alkali or detergent. According to a further inventive feature, a determination is made of the strength of the hydrogen peroxide or the concentration of the alkali or the concentration of acid. According to again another inventive feature, after the strength of the hydrogen peroxide or the concentration of alkali or acid has been determined, this strength or this concentration is compared with a predetermined value for the desired strength or concentration of the solvent involved and, when said value is not met, hydrogen peroxide or alkali or acid is added to the cleaning fluid until the relevant value has been reached while, when this value is exceeded, water is added until the predetermined value has been reached. The correct strength of the hydrogen peroxide, peracetic acid or concentration of the detergent is important for a proper cleaning because a lower strength or concentration than optimum decreases the cleaning functions whereupon high strength or concentration results in an unnecessarily high consumption of the solvent and burdening of environment.

According to again another inventive features, there is applied a method in which, after the milk line system has been rinsed with a cleaning fluid, the milk line system is post-rinsed with a post-rinsing fluid and during post-rinsing, the strength of the hydrogen peroxide or alkali or acid in the milk line system is determined and compared with a predetermined minimum value for the strength of the solvent being used and post-rinsing of the milk line system is only ended when the minimum strength has been reached. In this manner, residues of the cleaning fluid can be prevented from coming into the milk and affecting the quality thereof. The invention also relates to a method characterized in that the milk line system is rinsed with a calibration fluid containing a known strength of the hydrogen peroxide or alkali or acid and that this calibration value is compared with the strength of the hydrogen peroxide or alkali or acid measured in the milk line system and that, when the measured value deviates from the calibration valve, the means by which the electric conductivity of the fluid is measured is calibrated. In practice it has appeared that the aforementioned means show deviations after a period of time. These deviations may be caused by substances present in the milk, which deposit on the measuring means and which, during cleaning are insufficiently removed. Wear of the measuring means may also occur. By calibrating the measuring means again, it again may become possible to carry out a reliable measurement of the electric conductivity of the cleaning fluids. The invention furthermore relates to apparatus for applying a method as mentioned above, whereby the apparatus comprises a milk line system with one or more milk conductivity sensors included therein. In practice these milk conductivity sensors are used for checking the milk for mastitis. In the present invention, the milk conductivity sensors are utilized for another application, that is, for checking the cleaning of the milk line system.

In accordance with a further inventive feature, the apparatus comprises a milk line system in which one or more teat cups are included. According to again another inventive feature, there is disposed a milk conductivity sensor in the milk line of a teat cup. In a preferred embodiment according to the invention, each milk line that is connected to a teat cup is provided with a milk conductivity sensor. In this manner an optimum check of the cleaning of the milk lines of the teat cups can be carried out. In accordance with again another inventive feature, the apparatus comprises a milking robot for automatically connecting teat cups to the teats of an animal and after the teats involved have been milked, disconnecting them therefrom. The application of a method as described above in an apparatus including a milking robot and a milk line system has great advantages, because the milking robot operates for a relatively long period of time without human supervision and hence the cleaning of the milk line system is checked automatically without the presence of an operating person.

BRIEF DESCRIPTION OF THE DRAWINGS

For better understanding of the invention and to show how the same may be carried in to effect, reference will now be made, by way of example, to the embodiments presented in the accompanying FIG. 1, in which an apparatus for automatically milking animals is shown schematically, whereby only those parts of the apparatus are represented that are of importance for the understanding of the present invention.

DETAILED DESCRIPTION OF THE PREFERRED EMBODIMENTS

Figure 1:
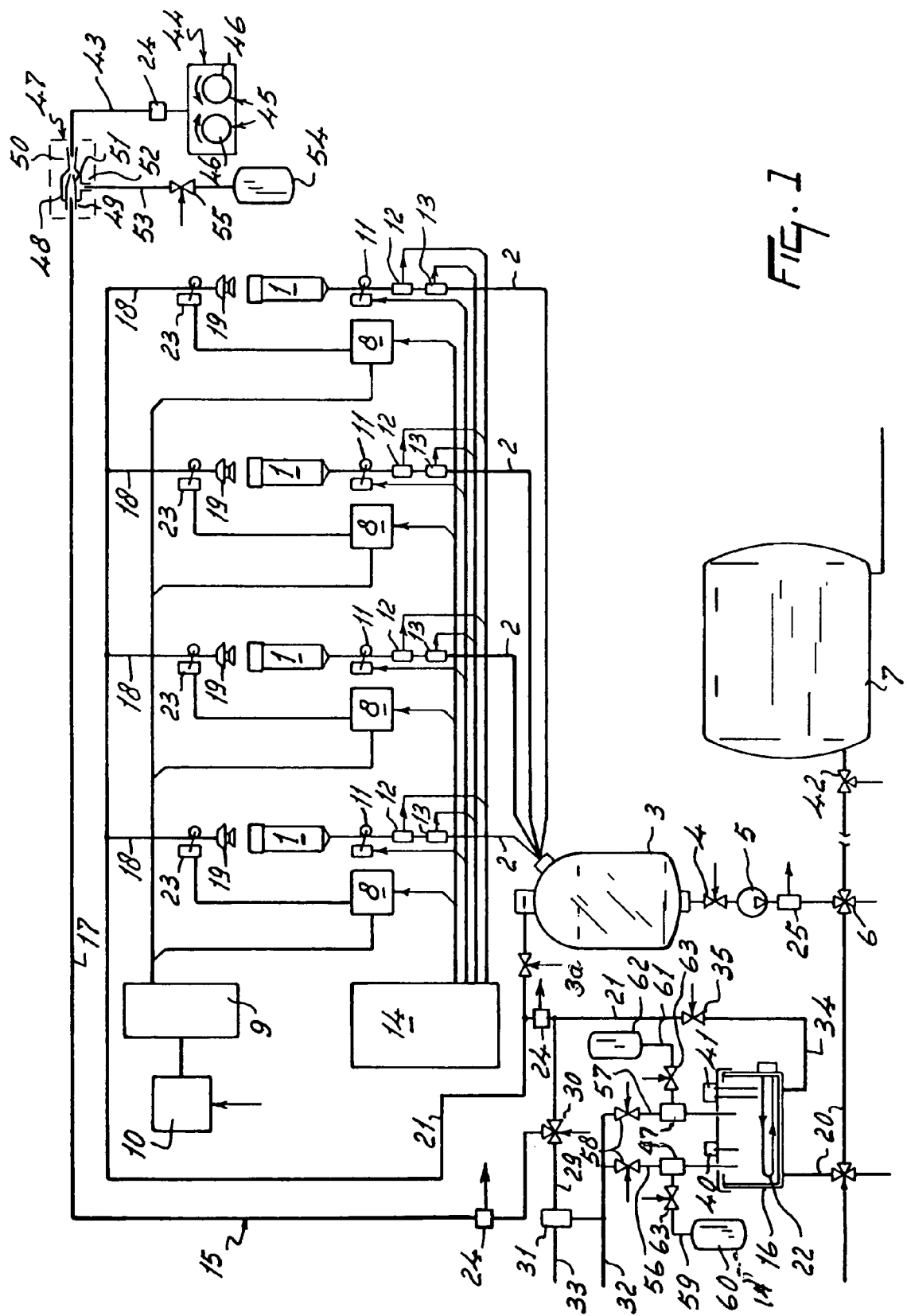

In the apparatus shown in FIG. 1, the teat cups are indicated by the reference numeral 1. These teat cups are each provided with a lining of flexible material, by means of which the teat space of a teat cup is separated from the pulsation space. By means of a milking robot, teat cups 1 can automatically be connected to the teats of an animal and upon completion of the milking process can be disconnected therefrom. To the teat space of each of teat cups 1 is connected a milk line 2. Each of milk lines 2 debouch into a milk glass 3. Via a valve 4, a pump 5 and a valve 6, milk glass 3 is in communication, inter alia, with a refrigerated bulk milk tank 7. A pulsator is provided for each of teat cups 1 applying pulsating vacuum in the pulsation space of and relevant teat cup 1. Each of the pulsators 8 is connected to a vacuum accumulator or vacuum balance tank 9, in which by means of a motor driven pump 10, a stabilized vacuum is generated. In each of milk lines 2 connected to teat cups 1 are consecutively close-off elements 11, vacuum sensors 12 and milk conductivity sensors 13. By means of milk conductivity sensors 13, the electric conductivity of the milk, cleaning and a rinsing fluids can be determined. Furthermore the apparatus comprises a computer 14, by means of which the various parts of the apparatus for automatically milking are controlled. For the purpose of rinsing, the apparatus is provided with a rinsing circuit which is generally identified by reference numeral 15, constituted by a rinsing fluid tank 16, a rinsing fluid supply line 17, separate rinsing fluid supply lines 18, each of which is connected to rinsing fluid lines 17 via lines 21 and 34. Fluid lines 18 are provided to rinsing jetters 19, connected to teat cups 1 for cleaning. It will be appreciated that tank 16 is elevated relative to lines 17 and 21. To obtain a closed rinsing circuit, milk glass 3 is capable of being connected, via the valve 6 and a return line 20, to rinsing fluid tank 16. By means of rinsing fluid line 21 there can furthermore directly be obtained, via a valve 3a, a shortened rinsing circuit through milk glass 3. In rinsing fluid line 21 there is further included a conductivity sensor 24, by means of which the electric conductivity of the rinsing fluid can be determined. By means of a heating element 22 in rinsing fluid tank 16, water containing a detergent, preferably heated to a temperature of 40° C. to 60° C., can be provided ultimately to be received by milk glass 3, via rinsing fluid line 21, the separate rinsing fluid supply lines 18, rinsing jetters 19, teat cups 1 and milk lines 2. This rinsing fluid is then pumped back, via valve 4, by means of pump 5 and via valve 6, to rinsing fluid tank 16. When the rinsing fluid is passed through the separate rinsing fluid supply lines 18, it may occur that the quantities of rinsing fluid, passing through the various teat cups, differ from each other to a considerable extent. Hence there is included a close-off element 23 in each of rinsing supply lines 18. Each close-off element 23 is under control of a corresponding pulsator 8. Pulsators 8 can be controlled by computer 14 in such a way that the close-off elements 23 connected to the relevant pulsators consecutively release and close off rinsing fluid supply lines 18, so that the rinsing fluid is passed, consecutively in time, through the respective teat cups 1. To optimize the rinsing of the teat cups, the temperature of the rinsing fluid is maintained as constant as possible during rinsing. For that purpose there is included a temperature sensor 25 in rinsing circuit 15. Said temperature sensor is in communication with computer 14, which controls heating element 22 in the rinsing tank.

In the apparatus, there is moreover connected to rinsing fluid supply line 17 a first supply line 29 for rinsing fluid, such as water. In first supply line 29, there is included a computer-controlled valve 30. To be able to control the temperature of the rinsing fluid, the first supply line 29 includes a thermostatically controlled tap 31, to which a hot water line 32 and a cold water line 33 are connected. By means of computer 14, for the purpose of pre-rinsing the milk lines, the teat cups and the milk glass, the thermostatically controlled tap 31 is adjusted to provide a temperature of the rinsing fluid of between 32° C. and 42° C. and preferably approximately 37° C. and computer-controlled valve 30 is opened for approximately five to seven minutes.

To the rinsing fluid line 17 there is furthermore connected a second supply line 34, extending from rinsing fluid tank 16, for a further rinsing fluid. Second supply line 34 also comprises a valve 35 controlled by computer 14.

As stated above, rinsing fluid tank 16 comprises a heating element 22, controlled by a thermostat 40, by means of which the water can be heated to a temperature approximately 78° C., which temperature is very suitable for heat cleaning. To prevent the rinsing fluid tank 16 from boiling dry, said rinsing fluid tank comprises fluid level pins 41 supplying a signal to computer 14 when there is no water in rinsing fluid tank 16 or the quantity of water therein is insufficient. Near milk glass 3, there is additionally included in the rinsing circuit a milk conductivity sensor 24, by means of which the electric conductivity of the rinsing fluid can be measured, which measurements are supplied to computer 14.

For discharging the rinsing fluid into the sewer, the rinsing circuit comprises two-way computer-controlled valve 42.

Computer-controlled valve 30 is designed as a three-way valve. To the rinsing fluid line there is connected a further rinsing fluid line 43 by means of which rinsing fluid conveyed via the first supply line 29 can be supplied to a cleaning device 44 for cleaning of cleaning elements 45, by means of which the udder or the teats or both of an animal are cleaned. In the further rinsing fluid line 43 there is also included in a milk conductivity sensor 24. In the present embodiment, cleaning elements 45 are designed as two spaced apart cleaning rollers 46, which, by means of a robot, can be brought under the animal's udder. During cleaning the teats are cleaned between the cleaning rollers 46 driven in opposite directions.

In rinsing fluid line 43 there is included a venture-element 47. Venture-element 47 comprises a cylindrical housing 48 including a supply nipple 49 and a discharge nipple 50. Supply nipple 49 extends into the cylindrical housing 48 to discharge nipple 50 and has a tapering end part 51. To cylindrical housing 48 there is connected, by means of a further nipple 52 and a further line 53, a tank 54 containing disinfecting fluid, such as chlorite. In the further line 53 there is included a computer-controlled valve 55. When it is desirable to clean the cleaning elements 45 with a chlorite-water mixture, such a mixture can be obtained by opening the computer-controlled valve 55. The water flowing through the venturi-element 47 provides a partial vacuum in cylindrical housing 48 so that the disinfecting fluid present in tank 54 is drawn into cylindrical housing 48 and is mixed with the water. By means of conductivity sensor 24 the concentration of the chlorite-water mixture can be checked.

Adding hydrogen peroxide, acid or alkali to rinsing fluid tank 16 is effected in a similar way as adding disinfecting fluid to the rinsing fluid line 43. For that purpose, line 32 branches off into a first line 56 and a second line 57, both debouching into rinsing fluid tank 16. In first line 56 and second line 57 each includes a venturi-element 47, while in both lines 56 and 57 there are included computer-controlled valves 58. To venturi-element 47 included in first line 56 there is connected, via a line 59, a tank 60 containing an alkaline fluid, while to venturi-element 47 included in the second line 57, there is connected via line 61, a tank 62 containing an acid. In lines 59 and 61 there are furthermore included computer-controlled valves 63. By means of conductivity sensor 24, included in the rinsing fluid line 17, the conductivity of the rinsing fluid can be determined. Then, by means of computer 14, the concentration of acid or alkali in the rinsing fluid can be determined. The concentration of acid or alkali in the rinsing fluid is also determined by means of milk conductivity sensors 13, which, near teat cups 1, are included in milk lines 2.

It will be appreciated by those skilled in the art that further tanks similar to tanks 60 and 62 may be added which contain other substances useful for sterilization of the milk line system and that such further tanks may be connected in the same manner as tanks 60 and 62 to discharge fluid into the rinsing fluid tank 16 including the computer-control valves such as valve 63 and venture-elements 47 to entrain to the substances into water from line 32 or line 33 or both. Such other sterilization or disinfectants fluids in the further containers may include hydrogen peroxide, peracetic acid, ozone, alcohols, aldehydes such as formaldehyde, phenol and ethylene oxide. In such cases the fluid should be such that it does not react adversely to materials it may encounter in the milk line system such as the teat cups or materials should be selected to avoid reacting with the cleaning fluids.

The use of hydrogen peroxide in agricultural farming has been increasing. For example it has been used for the fiber pre-digestion ruminant feed and in horticulture as an adjunct to foliar feeding, fertigation, irrigation, etc. It also can be used for water treatment including the treatment of household water supplies. It may further be used by being added to each field distribution piping to improve drainage systems and filtration through the soil. Calcium peroxide and magnesium peroxide have been used in bioremediation and composting operations as well as for coating seeds to improve germination and seedlings survival rates. Hydrogen peroxide is relatively inexpensive and is readily available from most industrial chemical distributors throughout the United States in various containers such as fifty-five gallon drums in concentrations of thirty-five or fifty percent by weight hydrogen peroxide. Pure hydrogen peroxide solutions including those which have been buffered are highly stable. An inhibitor such as acetanilide or sodium stannate may be added to counteract catalytic effects due to traces of impurities such as iron, copper and other heavy metals. A relatively stable sample of hydrogen peroxide typically decomposes at a rate of about 0.5 percent per year at room temperature.

In FIG. 1, either a second separate tank as indicated above or tank 60 can be used as a container for hydrogen peroxide at industrial concentration of thirty-five or fifty or even seventy percent hydrogen peroxide by weight. Acetic acid (vinegar) may be added directly to the hydrogen peroxide in tank 60 or mixed with water introduced via the venturi-element 47. Peracetic acid, as the active ingredient to make up five percent of the cleaning solution has a known capacity for disinfection/sterilization purposes in the food processing industry. However, whether the hydrogen peroxide, as such, or as a mixture of hydrogen peroxide with acetic acid, the proportion of the hydrogen peroxide or peracetic acid should be as low as possible while, at the same time, providing adequate disinfection/sterilization of the milk line system and equipment therein. Hydrogen peroxide and peracetic acids are powerful anti-microbial agents and effective sporicides. As indicated above, a thirty-five weight percent solution of hydrogen peroxide can be stored for prolonged periods, is easy to handle, is non-corrosive, and mixes readily with water. An important advantage of hydrogen peroxide in sterilization is that it decomposes to oxygen and water, thus presenting no disposal problems. The ratio of hydrogen peroxide or peracetic acid or both to water, provided by the venturi-element 47 will vary according to the circumstances depending upon the quality and composition of the water, the geometry and extent of the milk line system, and the temperature, both ambient and also of the cleaning fluid, as such. However, in general, it will be within a range of three to eight percent by weight.

Instead of a tank 60 or, in supplement to such tank an apparatus for producing hydrogen peroxide from water available at the dairy farm may be provided. However, such water should preferably be quite pure although this is much less important if the output of the apparatus is used soon after its production such as daily or every other day. Although such an apparatus can be controlled manually, preferably it is controlled by a computer such as computer 14 as indicated by the dashed leadline in FIG. 1 from tank 60. In this case tank 60 is considered as an apparatus 60 for producing hydrogen peroxide. Virtually all commercial productions of hydrogen peroxide utilize presently a process based on the auto-oxidation of anthraquinones. (See e.g. U.S. Pat. No. 2,059,569). However, from the 1920's through the 1950's, the primary production method was electrolytic. In the electrolytic method, aqueous sulfuric acid or acidic ammonium bisulfate is converted to electrolytically to pure peroxydisulfate which is hydrolyzed to form hydrogen peroxide. Patents which disclose various processes for electrolytically producing hydrogen peroxide are: U.S. Pat. No. 916,900 of Teichner, U.S. Pat. No. 959,605 of Quesisser, U.S. Pat. No. 975,354 of Grutet et al, U.S. Pat. No. 1,234 of Patek, U.S. Pat. No. 2,000,815 to Berl, U.S. Pat. No. 2,022,650 to Dawsey and U.S. Pat. No. 3,856,640 to Halfar et al. These disclosures are incorporated by reference and it will be appreciated by those skilled in the art that such and similar processes can be readily controlled by computer programs.

Although I have disclosed the preferred embodiments of my invention, it is to be understood that it is capable of further adaptations and modifications within the scope of the appended claims.

The invention claimed is:

1. A method of testing at least two distinctive ionic conductive liquids flowing in a milk line system at different times comprising measuring the flow of electrical current between a pair of electrodes in said system when said liquid is milk to determine the wholesomeness of the milk and, when the liquid is a fluid that contains hydrogen peroxide, to determine the completeness of the rinsing process in said milk line system.

2. A method in accordance with claim 1, wherein said milk line system includes a plurality of teat cups, milk from each said teat cup being received in a separate milk line, further electrodes comprising a further pair of electrodes in each said milk line, each said pair of electrodes separately transmitting data to a computer as to the wholesomeness of milk in each corresponding said milk line during the milking operation and further transmitting data to said computer during a rinsing operation concerning the completeness of the rinsing process of each said milk line.

3. A method in accordance with claim 2, including the step of securing all but one of said milk lines during the rinsing operation so that only one of said milk lines is being rinsed at a time in succession.

4. A method in accordance with claim 1, comprising maintaining the temperature of said rinsing fluid at a constant temperature during the milking operation.

* * * * *